United States Patent [19]
Murad

[11] Patent Number: 5,962,517
[45] Date of Patent: *Oct. 5, 1999

[54] PHARMACEUTICAL COMPOSITIONS AND METHODS FOR TREATING ACNE

[76] Inventor: Howard Murad, 4316 Marina City Dr., Marina del Rey, Calif. 90292

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/016,800

[22] Filed: Jan. 30, 1998

Related U.S. Application Data

[60] Provisional application No. 60/036,825, Jan. 31, 1997.
[51] Int. Cl.$^6$ ........................ A61K 31/715; A61K 31/34; A61K 31/19
[52] U.S. Cl. ........................... 514/474; 514/557; 514/801; 514/474; 514/62; 514/54; 514/859; 514/188; 424/417
[58] Field of Search .................................. 514/188, 859, 514/310, 557, 801, 474, 62, 54; 424/417

[56] References Cited

U.S. PATENT DOCUMENTS

| | | | |
|---|---|---|---|
| 5,294,606 | 3/1994 | Hastings | 514/53 |
| 5,496,827 | 3/1996 | Patrick | 514/310 |
| 5,654,286 | 8/1997 | Hostetler | 514/47 |
| 5,741,212 | 4/1998 | Matthews | 600/300 |
| 5,804,594 | 9/1998 | Murad | 514/474 |
| 5,834,409 | 11/1998 | Ramachandran et al. | 510/125 |
| 5,834,480 | 11/1998 | Elkhoury | 514/289 |

OTHER PUBLICATIONS

Pizzorno, Joseph E., Jr.:10 drugs I would never take . . . – Natural health, p82(9), 1996.

Murray, Frank: Looking below the surface of skin disorders.–Better Nutri. f/Todays Living, p52(3), 1994.

Whitaker, Julian:Dr. Whitaker's guide to natural healing–Prima publishing, 1995.

Davis et al, The influence of Keratin on . . . , Proc. SPIE–Int. Soc. opt. Eng., vol. 2679, p216–226, 1996.

C. Macek, "Synthetic vitamin A analogue (isotretinoil) waiting for approval for cystic acne therapy", *Medical News*, 247(13): 1800–1801 (Apr. 1982).

D. Mowry, *The Scientific Validation of Herbal Medicine*, 32–33; 247–251; 248 (1986).

B. Idson, "Vitamins in Cosmetics, An Update", *Drug & Cosmetic Industry* (May 1990).

D. Zafirov, et al., "Antiexudative and capillaritonic effects of procyanidines isolated from grape seeds (V. Vinifera)", *Acta Physiologica et Pharmacologica Bulgarica*, 16(3):50–4 (1990).

A. Reinberg, et al. "Day–night differences in effects of cosmetic treatments on facial skin. Effects on facial skin appearance.", *Chronobiology International*, 7(1):69–79 (1990).

P. Poshi, et al., "Report of the Concensus Conference on Acne Classification", *J. Amer. Acad. Derm.*, 24(3):1–6 (Mar. 1991).

GP. Deucher, "Antioxidant therapy in the aging process", *Free Radicals and Aging*, 62:428–37 (1992).

B. Xie, et al., "Antioxidant properties of fractions and polyphenol constituents from green, oolong and black teas", *Proceedings of the National Science Council, Republic of China. Part B, Life Sciences*, 17(2):77–84 (Apr. 1993).

R. Agarwal, et al., "Protection against ultraviolet B radiation–induced effects in the skin of SKH–1 hairless mice by a polyhenolic fraction isolated from green tea", *Photochemistry and Photobiology*, 58(5):695–700 (Nov. 1993).

H. Trachtman, et al.; "Taurine prevents glucose–induced lipid peroxidation and increased collagen production in cultured rat mesangial cells", *Biochemical and Biophysical Research Communications*, 191(2):759–65 (Mar. 1993).

R. Maffei Facino, et al., "Free radicals scavenging action and anti–enzyme activities of procyanides from Vitis vinifera. A mechanism for their capillary protective action", *Arzneimittel-Forschung* 44(1):594–601 (May 1994).

J. Whitaker, *Dr. Whitaker's Guide to Natural Healing*, Prince Publishing, 141–142 (1995).

R. Swain & B. Kaplan, "Vitamins as Therapy in the 1990's", *J. Am. Board Fam. Pract.* 8:206–216 (1995).

Roche Laboratories Inc., *Important Information Concerning Your Treatment with Accutane*, 6th ed. (1996).

Dr. M. Tierra, *Planetary Herbology*, Lotus Press, 153–154;157–160.

*Primary Examiner*—Keith D. MacMillan
*Assistant Examiner*—Vickie Kim
*Attorney, Agent, or Firm*—Pennie & Edmonds LLP

[57] ABSTRACT

This invention relates to a pharmaceutical composition for the treatment of acne having an acne reduction component in an amount sufficient to reduce the redness and blemishes associated with acne. The invention also relates to pharmaceutical compositions having, in addition to the acne reduction component, a skin cell conditioning component in an amount sufficient to properly regulate the keratin and sebum production of the skin cells, thereby inhibiting the appearance of acne. In a preferred form, the skin cell conditioning component is a chromium component. In another preferred form, the composition further includes at least one of a vitamin C source, burdock root, yellow dock root, horsetail extract, a catechin-based composition, a vitamin $B_1$ source, a vitamin $B_2$ source, a vitamin $B_3$ source, a vitamin $B_5$ source, and a vitamin E source. In a more preferred form, the invention also includes at least one amino acid component, a magnesium component, a selenium component, and biotin. The invention also relates to methods for treating acne by administering, alone or in conjunction with another composition, the pharmaceutical compositions in an amount therapeutically effective in reducing the incidence of acne and methods for additionally inhibiting the appearance of acne by conditioning skin cells.

21 Claims, No Drawings

PHARMACEUTICAL COMPOSITIONS AND METHODS FOR TREATING ACNE

CROSS-REFERENCE TO RELATED APPLICATIONS

This application claims priority to provisional Application No. 60/036,825, filed Jan. 31, 1997.

TECHNICAL FIELD

This invention relates to pharmaceutical compositions for treating acne and conditioning the skin cells in patients. The invention further relates to methods of treating acne and conditioning skin cells by administering the pharmaceutical compositions to the patient.

BACKGROUND OF THE INVENTION

The mammalian skin, in particular, human skin, is a multifunctional organ. Not only does the skin provide an external covering to protect the body, but it also performs several specialized functions, such as breathing, perspiring, sensory information processing, and oil production. [D. Mowery, *The Scientific Validation of Herbal Medicine*, 248 (1986)]. Oil production, essential to the protective features of the skin, works when an oily substance known as sebum is released from the sebaceous glands, which are large glands located at the base of a hair follicle. This permits the skin to moisturize and waterproof itself, thereby protecting itself from the environment. [J. Whitaker, *Dr. Whitaker's Guide to Natural Healing*, 141, (1995)].

Unfortunately, puberty adversely affects the production of sebum, which in some cases is caused by increased levels of testosterone in both males and females. For example, testosterone stimulates the sebaceous glands accompanying the hair follicles. In response, these glands become enlarged and begin to secrete more sebum than usual. Also, testosterone causes the cells lining a pore to release more keratin, an insoluble protein that is the primary constituent of the hair and the epidermis. Together, the sebum and keratin block a skin pore, resulting in a comedone, also known as a blackhead. Bacteria proliferates in clogged pores, and the body typically responds by releasing enzymes to breakdown the sebum. The enzymes cause the pore to become inflamed. This eventually may result in pustules or pimples. This condition is typically known as acne vulgaris. [Id.]. This response is especially prevalent on the face, back, and shoulders, where a greater amount of sebaceous glands exist.

Acne conglobate, more commonly known as nodular or cystic acne, is a more severe form of acne than acne vulgaris. In the case of nodular acne, the sebum builds up in the gland, mixes with dead cells, and eventually ruptures the follicle wall, which typically forms a deep cyst under the skin. Scarring often results from these deep cysts. [Roche Laboratories Inc., *Important Information Concerning Your Treatment with Accutane*, 6th ed., (1996)]. Also, acne not only affects a person's appearance, but sometimes has detrimental affects on the person's psychological, social, and occupational status. [P. Poshi, et. al., *Report of the Consensus Conference on Acne Classification*, J. Amer. Acad. Derm., 24/3/1–6 (March 1991)]. Present methods of treating acne attempt to address the three separate causes of acne: excess sebum production, keratinization disorders, and increases in the bacteria *Propionibacterium acnes*. [R. Swain & B. Kaplan, *Vitamins as Therapy in the 1990's*, J. Am. Board Fam. Pract. 8:206–216 (1995)].

Non-vitamin methods of addressing acne commonly attempt to curb acne by mitigating the sebum production through drying agents, such as alcohol and benzoyl peroxide. Additionally, antibiotics, applied topically or orally, such as benzoyl peroxide, erythromycin, clindamycin, or tetracycline are commonly used to control the bacteria. These methods often lead to overly dry skin, and relapse is common after treatment has ended. [Id.].

Vitamins and herbs often provide more promising results with regard to acne. Vitamin A has proven to be highly effective in treating acne. Since the early seventies, topical retinoic acid or tretinoin, both derivatives of vitamin A, have been used to treat acne topically. [Id.]. These topical agents work by normalizing the skin's production of keratin and the sebaceous glands production of sebum, thereby preventing obstruction of the follicle. Although highly effective, the benefits of the topical treatment often take several weeks. Also, the patient's condition may become worse before clearing up. Finally, these topical treatments tend to have mild side effects, which include stinging and reddening of the treated areas and possible photosensitivity. [Id. at 207].

A systemic vitamin A derivative for the treatment of nodular acne, known as isotretinoin, is commercially available under the name ACCUTANE®, from Roche Laboratories in Nutley, N.J. It has been found that treatment using isotretinoin can clear up as much as 85 percent of the acne over a 4 to 6 month period. [Id.]. Also, the patient's condition tends to improve even after the treatment has ceased. Unfortunately, side effects often result from treatment using isotretinoin, and patients need to be monitored carefully. Monthly testing of the patient's liver, lipids and glucose is necessary to monitor the response to isotretinoin. The side effects are often mucocutaneous: cheilitis (dry, blistering lips), dry eyes or nose, eye irritation, pruritus, epistaxis (nosebleed), mild alopecia (hair loss), and some photosensitivity. [Id.]. Furthermore, isotretinoin is teratogenic, and therefore posses a serious risk of causing birth defects in pregnant women. Birth defects such as craniofacial, cardiac, and central nervous system abnormalities may result from even small amounts of isotretinoin taken over short periods of time. Thus, doctors administering this treatment often require females to take effective contraception prior to, during, and after treatment. [Roche Laboratories Inc., *Important Information Concerning Your Treatment with Accutane*, 6th ed., (1996)].

Other minerals and vitamins are also thought to be effective in treating acne. Zinc is believed to be useful in the treatment of acne, because of its ability to aid in wound healing, immune response, inflammation control, tissue regeneration, and more effective utilization of vitamin A. Certain studies have shown that zinc produces results similar to tetracycline in the treatment of superficial acne, but far superior results with regard to deeper forms of acne. [J. Whitaker, *Dr. Whitaker's Guide to Natural Healing*, 142 (1995)]. Also, certain nutrients, such as vitamin $B_6$, selenium, and vitamin E, are thought necessary to healthy skin and, therefore, control acne. [Id.].

Also, herbs, such as sassafras and elder flowers, used both individually and in conjunction have been suspected of providing effective acne treatment. [M. Tierra, *Planetary Herbology*, 154 & 158 (1988)]. Additionally, herbs possessing antibiotic properties, such as burdock root and horsetail, may individually aid in the treatment of skin blemishes, such as acne. [D. Mowery, *The Scientific Validation of Herbal Medicine*, 32–33 (1986)].

Several acne treatments exist that utilize the above vitamins, minerals, and herbs. AKNE-ZYME™, a nutritional supplement produced by one company, has been used in conjunction with a cleanser and topical cream to treat acne. The nutritional supplement contains zinc, vitamin A, vitamin C, and other natural elements that are believed to nourish the skin. Also, it is suggested that high doses of vitamin A are not needed in AKNE-ZYME™ as long as other nutritional factors such as zinc, vitamin $B_6$, selenium, and vitamin E are incorporated into the acne treatment. [J. Whitaker, *Dr. Whitaker's Guide to Natural Healing*, 141–142 (1995)].

Also, an herbal treatment for acne has been suggested in *The Scientific Validation of Herbal Medicine*. [D. Mowery, 247–51 (1986)]. The herbal treatment includes the following: chaparral, dandelion root, burdock root, licorice root, echinacea, yellow dock root, kelp, and cayenne. It is suggested therein that the herbal extract be used in conjunction with supplements of one or more of the following nutrients and minerals: vitamin A, vitamin $B_1$, vitamin $B_2$, vitamin $B_6$, vitamin B complex, vitamin C, vitamin D, vitamin E, niacinamide, pantothenic acid, para-aminobenzoic acid, biotin, choline, inositol, folic acid, zinc, calcium, magnesium, and potassium. The reference further notes the possible use of the herbal supplement with a detoxifying herbal supplement, which contains burdock root and horsetail. [Id. at 32–33 and 148].

Although the above references disclose methods of treating acne, the treatments often involve adverse side effects, such as overdrying of the skin. Furthermore, the above treatments simply address the acne and fail to condition the skin cells to assist in the treatment and to reduce further incidences of acne. Thus, it is desired to find pharmaceutical compositions and methods for treating acne by administering the pharmaceutical compositions and conditioning the skin to inhibit further acne outbreaks without the adverse side effects present in many conventional acne treatments. The present invention, through a blend of herbal extracts and nutritional supplements, advantageously treats acne without adverse side effects, and conditions skin cells to reduce the likelihood of further acne.

SUMMARY OF THE INVENTION

The present invention relates to a pharmaceutical composition for the treatment of acne comprising an acne reduction component in an amount sufficient to reduce the redness and blemishes associated with acne and a skin cell conditioning component in an amount sufficient to properly regulate the keratin and sebum production of the skin cells to inhibit the appearance of acne.

The skin cell conditioning component comprises a transition metal complex with an organic compound. In a preferred embodiment, the transition metal is complexed to a nitrogen containing aromatic compound. In the more preferred embodiment, the transition metal comprises chromium and the complex is present in about 0.001 to 5 weight percent of the pharmaceutical composition.

The acne reduction component is a vitamin A source, a carotenoid component, a vitamin $B_6$ source, and a zinc component. In a preferred embodiment, the vitamin A source is vitamin A complexed with an acetate or palmitate, the carotenoid component is beta-carotene, the vitamin $B_6$ source is a pyridoxine, and the zinc component is zinc complexed with ascorbic acid or ascorbate. In a more preferred embodiment, the vitamin A source is vitamin A palmitate present in about 0.005 to 5 weight percent, beta-carotene is present in about 0.1 to 10 weight percent, the pyridoxine is pyridoxine hydrochloride present in about 0.2 to 20 weight percent, and the zinc component is zinc ascorbate present in about 0.1 to 25 weight percent of the pharmaceutical composition.

In one embodiment, the composition further contains a pharmaceutically acceptable carrier or excipient.

Another embodiment of the pharmaceutical composition also has at least one of a vitamin C source, burdock root, yellow dock root, horsetail extract, a catechin-based composition, a vitamin $B_1$ source, a vitamin $B_2$ source, a vitamin $B_3$ source, a vitamin $B_5$ source, and a vitamin E source, all in an amount sufficient to facilitate maintenance of skin cells. In a preferred embodiment, the vitamin C source is ascorbic acid or ascorbate, the catechin-based composition is a proanthanol or proanthocyanidin, the vitamin $B_1$ source is thiamin, the vitamin $B_2$ source is riboflavin, the vitamin $B_3$ source is niacinamide, the vitamin $B_5$ source is pantothenic acid, and the vitamin E source is a sulfate or succinate vitamin E complex. In a more preferred embodiment, the vitamin C source is calcium ascorbate present in about 1 to 30 weight percent, the burdock root is present in about 1 to 30 weight percent, the yellow dock root is present in about 1 to 20 weight percent, the horsetail extract is present in about 1 to 20 weight percent, the catechin-based composition is proanthocyanidin present in about 0.1 to 15 weight percent, the niacinamide is present in about 0.05 to 5 weight percent, the pantothenic acid is present in about 0.05 to 5 weight percent, the riboflavin is present in about 0.05 to 5 weight percent, the thiamin is present in about 0.05 to 5 weight percent and the vitamin E source is vitamin E succinate present in about 1 to 30 weight percent.

In another embodiment, the pharmaceutical also has at least one amino acid component, a magnesium component, a selenium component, and biotin in an amount sufficient to facilitate repair of skin damaged by acne. In a preferred embodiment, the amino acid component is L-lysine and L-proline, the magnesium component is magnesium oxide, and the selenium component is selenium complexed to an amino acid. In a more preferred embodiment, the L-lysine is L-lysine hydrochloride and the L-lysine hydrochloride and proline are together present in about 1 to 30 weight percent, magnesium oxide is present in about 1 to 20 weight percent, the selenium component is L-selenomethionine present in about 0.05 to 10 weight percent, and biotin is present in about 0.01 to 5 weight percent of the pharmaceutical composition.

The invention also relates to a method for treating acne by orally administering one of these pharmaceutical compositions in an amount therapeutically effective to reduce the redness and blemishes associated with acne. In addition, the invention relates to a method for conditioning skin cells in a treatment for acne, by administering these pharmaceutical compositions in an amount therapeutically effective to condition the skin to assist in reducing the redness and blemishes associated with acne.

In a preferred embodiment, the composition is administered orally. In one embodiment, the composition is administered as a tablet or capsule having about 1 mg to 2,500 mg of composition. In a preferred embodiment, the tablet or capsule has about 400 mg to 2,000 mg of composition. In a more preferred embodiment, the tablet or capsule has about 800 mg to 1,600 mg of composition.

In another embodiment, the composition is administered in conjunction with concurrent or subsequent treatment by at least an additional pharmaceutical composition used to treat acne or condition the skin. In a preferred embodiment, the additional pharmaceutical composition is a topical application having at least one of: alcohol, benzoyl peroxide, erythromycin, clindamycin, tretinoin, vitamin E, and vitamin A or its derivatives; or an oral application having at least one of: erythromycin, tetracycline, isotretinoin, vitamin C, vitamin D, chaparral, dandelion root, licorice root, echinacea, kelp, cayenne, sassafras, elder flowers, pantothenic acid, para-aminobenzoic acid, biotin, choline, inositol, folic acid, calcium, magnesium, potassium and Vitamin A derivatives.

DETAILED DESCRIPTION OF THE PREFERRED EMBODIMENTS

A pharmaceutical composition for treating acne and conditioning the skin cells has now been discovered. The pharmaceutical composition includes an acne reducing component in an amount sufficient to reduce the redness and blemishes associated with acne. Additionally, the present invention preferably includes a skin cell conditioning component in an amount sufficient to properly regulate the keratin and sebum production of the skin cells, thereby inhibiting or preventing the appearance of acne. The present pharmaceutical composition advantageously treats acne and conditions skin cells with reduced adverse side effects compared to conventional acne compositions and treatment methods. Also, the present invention relates to a method of treating acne using the present pharmaceutical composition, alone or in conjunction with other pharmaceutical compositions.

The present invention reduces acne in a patient by providing an acne reduction component that includes at least one of a vitamin A source, a carotenoid component, a vitamin $B_6$ source, and a zinc component, in an amount sufficient to reduce the redness and blemishes associated with acne. Preferably, all four ingredients are present in the pharmaceutical composition. The acne reducing component may be administered by any method, although oral administration is preferred.

The zinc component of the pharmaceutical composition reduces the inflammation associated with acne. Furthermore, the ability of zinc to aid in wound healing, immune response, tissue regeneration, and utilization of vitamin A make it an effective component in the composition and for the treatment of acne according to the invention. The zinc component may be any zinc compound or pharmaceutically acceptable salt thereof, but preferably is a zinc complex with ascorbic acid or ascorbate, and more preferably is zinc ascorbate, wherein the zinc is typically present in about 5 to 30 weight percent of the complex. The zinc component is present in about 0.1 to 25 weight percent, preferably 0.5 to 8 weight percent, and more preferably about 1 to 6 weight percent of the pharmaceutical composition. A unit dose of the zinc component is typically about 6 mg to 96 mg, preferably about 10 mg to 76 mg, and more preferably about 15 mg to 56 mg. Although increasing amounts are more effective in treating acne, too great an increase in the zinc concentration within an orally formulated pharmaceutical composition may lead to stomach discomfort.

Vitamin A is necessary for healthy skin cell growth and tissue formation. Its function is to inhibit the production of excess skin cells that eventually flake off and tend to clog pores. The vitamin A source preferably is vitamin A complexed to an acetate or palmitate, and more preferably is vitamin A palmitate. The vitamin A source is present in about 0.005 to 5 weight percent, preferably in about 0.07 to 3 weight percent, more preferably in about 0.1 to 2 weight percent of the composition. A unit dose of the vitamin A source is typically about 0.1 to 5 mg, preferably about 0.5 to 4 mg, and more preferably is about 1 to 3 mg. Vitamin A is toxic at high levels, such that if vitamin A is taken in doses of more than 50,000 IU per day over a period of several months it can produce toxic effects in adults.

The carotenoid component used in the invention includes at least one powerful antioxidant, such as beta-carotene, canthaxanthin, zeaxanthin, lycopen, lutein, crocetin, and capsanthin. Beta-carotene is a carotenoid that is predominantly found in the skin. Beta-carotene protects the integrity of the skin cells' structure, fights various skin conditions, and enhances the immune system. Carotenoids, preferably beta-carotene, are present in the pharmaceutical composition at about 0.1 to 10 weight percent, preferably about 0.2 to 5 weight percent, and more preferably about 0.3 to 3 weight percent. A unit dose of the carotenoid component is typically about 2.5 to 40 mg, preferably about 5 to 25 mg, and more preferably about 7.5 to 18 mg.

A vitamin $B_6$ source is used in the creation of amino acids necessary for the production of collagen. The Vitamin $B_6$ complex actually includes closely related groups of substances commonly known as pyridoxine, pyridoxal, and pyridoxamine, any of which are suitable. Preferably, the source of vitamin $B_6$ is pyridoxine, and more preferably the source is pyridoxine hydrochloride. The vitamin $B_6$ source is present in the pharmaceutical composition at about 0.2 to 20 weight percent, preferably about 0.3 to 5 weight percent, and more preferably about 0.4 to 2 weight percent of the pharmaceutical composition. A unit dose of the vitamin $B_6$ source is typically about 4 mg to 70 mg, preferably about 8 mg to 50 mg, and more preferably about 10 mg to 30 mg.

The present invention, in addition to the acne reducing component, preferably contains a skin cell conditioning component in an amount sufficient to properly regulate the sebum in the sebaceous glands and keratin production of the skin cells. This preferred embodiment of the pharmaceutical composition may be administered by any means, although oral administration is preferred.

The skin cell conditioning component activates enzymes that are involved in fat and glucose metabolism, which assists the skin cells in regulating the production of keratin and sebum. These enzymes increase the glucose intake of cells, thereby increasing the operating efficiency of those cells. Thus, the present invention attempts to prevent further acne breakouts by encouraging optimal performance of the sebaceous glands. Preferably, the skin cell conditioning component is a transition metal complex with an organic compound. Any transition metal can be used but those of Groups 4b, 5b, 6b and 7b of the periodic table are preferred. The most preferred transition metals include those of column 5b and 6b, with vanadium and chromium being advantageous.

Preferably, the transition metal is complexed to a nitrogen-containing aromatic compound. Typical nitrogen-containing aromatic compounds include picolinates, nicotinates, pyridines, lutidines, collidinse, quinolines, isoquinolines, and diazines. The optimum complex is at least one of chromium polynicotinate and chromium picolinate.

The skin cell conditioning component is present in about 0.001 to 5 weight percent, preferably about 0.002 to 3 weight percent, and more preferably about 0.005 to 1 weight percent of the pharmaceutical composition. A unit dose of the skin cell conditioning, such as a chromium component, is about 0.01 mg to 24 mg, preferably about 0.03 mg to 18 mg, and more preferably about 0.06 mg to 12 mg.

The present invention more preferably contains at least one of the following: a vitamin C source, burdock root, yellow dock root, horsetail extract, a catechin-based component, a vitamin $B_3$ source, a vitamin $B_5$ source, a vitamin $B_2$ source, and a vitamin E source to aid in the maintenance of the skin cells.

The pharmaceutical composition includes a vitamin C source that includes an ascorbic acid, or pharmaceutically acceptable salt or ester thereof, and preferably includes ascorbyl palmitate, dipalmitate L-ascorbate, sodium L-ascorbate-2-sulfate, or an ascorbic salt, such as sodium, potassium, and calcium, or mixtures thereof. More preferably, the acceptable salt is calcium ascorbate. When oral formulations of the pharmaceutical composition are used, it is preferred that a non-acidic form of vitamin C be used to reduce the stomach irritation that may occur when using an acidic form. The vitamin C source is present in the pharmaceutical composition in about 1 to 30 weight percent, preferably about 5 to 25 weight percent, and more preferably about 10 to 20 weight percent. A unit dose of this vitamin C source is typically about 50 mg to 800 mg, preferably about 60 mg to 600 mg, and more preferably about 80 mg to 400 mg.

Burdock root, whose scientific name is *Arctium lappa*, acts as a cleanser and purifier. The herb contains insulin as an active ingredient. Burdock root is present in about 1 to 30 weight percent, preferably about 3 to 25 weight percent, and more preferably about 6 to 20 weight percent of the pharmaceutical composition. A unit dose of burdock root is typically about 50 mg to 600 mg, preferably about 75 mg to 450 mg, and more preferably about 100 mg to 300 mg.

Yellow Dock, whose scientific name is Rumex crispus, is often used to treat skin disease, especially those involving some form of inflammation. The active constituents of yellow dock are rumicin and chrysarobin. Yellow Dock extract is present in the pharmaceutical composition in about 1 to 30 weight percent, preferably about 3 to 25 weight percent, and more preferably about 5 to 20 weight percent. A unit dose of yellow dock is typically about 50 mg to 600 mg, preferably about 75 mg to 450 mg, and more preferably about 100 mg to 300 mg.

Horsetail is an herbal extract that contains silica, starch, volatile oils, resin, and equisetic acid as active components. This herbal extract aids in detoxifying the skin, and also possesses antibiotic properties. Horsetail extract is present in about 1 to 20 weight percent, preferably about 2 to 15 weight percent, and more preferably about 4 to 12 weight percent of the pharmaceutical composition. A unit dose of horsetail extract is typically about 25 mg to 400 mg, preferably about 50 mg to 300 mg, and more preferably about 75 mg to 200 mg.

The catechin-based preparation contained within the pharmaceutical composition provides powerful antioxidants to scavenge free radicals. These antioxidants are approximately 20 times more effective than vitamin C and approximately 50 times more effective than vitamin E in scavenging free radicals to prevent the skin from being damaged. The catechin-based preparation is preferably a proanthanol or a proanthocyanidin, more preferably a proanthanol, and most preferably grape seed extract. The catechin-based preparation is typically present in about 0.1 to 15 weight percent, preferably about 0.2 to 5 weight percent, and more preferably about 0.3 to 2 weight percent of the pharmaceutical composition. A unit dose of the catechin-based preparation is typically about 3 mg to 50 mg, preferably about 5 mg to 40 mg, and more preferably about 7 mg to 30 mg.

The present invention also optionally includes several vitamin B sources. Vitamin $B_1$, also commonly known as thiamine, aids carbohydrate metabolism, as well as the growth and maintenance of healthy skin. Both vitamin $B_2$ and $B_3$ are involved in tissue repair. Vitamin $B_2$, also commonly known as riboflavin, is involved in both the protein and the liquid metabolism necessary to rebuild damaged skin tissues. Moreover, Vitamin $B_3$ acts as a vasodilator, increasing the blood flow to the skin and other tissues. Vitamin $B_3$ includes several vitamin B complexes, such as niacin, nicotinic acid, niacinamide, and nicotinamide. Preferably, niacinamide is used in the present invention. Vitamin $B_5$ complex also aids in several metabolic functions. All of the above vitamin B complexes also enhance the effectiveness of vitamin $B_6$ in treating the skin. Preferably, the $B_5$ source is pantothenic acid. Each of these vitamin B complexes may be found in the present pharmaceutical composition in about 0.05 to 15 weight percent, preferably about 0.2 to 5 weight percent, and more preferably about 0.3 to 3 weight percent. A unit dose of the above vitamin B complexes is typically about 1 mg to 50 mg, preferably about 1.5 mg to 35 mg, and more preferably about 2 mg to 20 mg.

Also, a vitamin E source, which maintains the strength and proper functioning of cells and skin tissue membranes, may be included in the present invention. The vitamin E source is preferably a sulfate or succinate vitamin E complex, more preferably a D-alpha tocopherol acid succinate. The vitamin E source is present in about 1 to 30 weight percent, preferably about 6 to 25 weight percent, and more preferably about 7 to 20 weight percent of the pharmaceutical composition. The unit dose of the vitamin E source is typically about 40 mg to 650 mg, preferably about 60 mg to 500 mg, and more preferably about 80 mg to 350 mg.

Also, the present invention most preferably includes at least one of an amino acid component, a selenium component, a magnesium component, and biotin to aid in repairing the damage caused by acne although these ingredients are optional.

These ingredients preferably include at least one amino acid to assist in repairing acne damage to the skin. Preferably, two or more amino acids are used. Lysine and proline are the most preferred amino acids and are advantageously used in combination. Cysteine, methionine, or other amino acids may also be used, if desired. The amino acids may be used in a soluble form, such as the hydrochloride, i.e., L-lysine hydrochloride. The amino acids are present in an amount of about 1 to 30 weight percent, preferably about 3 to 25 weight percent, and more preferably about 5 to 20 weight percent of the pharmaceutical composition. A unit dose of the amino acids is typically about 40 mg to 650 mg, preferably about 60 mg to 500 mg, and more preferably about 80 mg to 350 mg.

Additionally, a selenium component may be added to the pharmaceutical composition. A selenium compound or pharmaceutically acceptable salt thereof may be used. Preferably, the selenium compound is complexed with an amino acid. More preferably, the selenium compound is L-selenomethionine, wherein the selenium is present in about 0.1 to 5 weight percent of the complex. Selenomethionine is present in the pharmaceutical composition at about 0.05 to 10 weight percent, preferably about 0.1 to 5 weight percent, and more preferably about 0.3 to 3 weight percent. A unit dose of the selenium component is typically about 2 mg to 40 mg, preferably about 4 mg to 30 mg, and more preferably about 6 mg to 20 mg.

The magnesium component may be any magnesium compound or pharmaceutically acceptable salt thereof, but preferably is a magnesium oxide complex, wherein the magnesium is typically present in about 20 to 70 weight percent of the complex. The magnesium component is present in the pharmaceutical composition at about 1 to 20 weight percent, preferably about 2 to 17 weight percent, and more preferably about 3 to 14 weight percent. A unit dose of the magnesium component is typically about 25 mg to 400 mg, preferably about 50 mg to 300 mg, and more preferably about 75 mg to 200 mg.

Also, biotin may advantageously be added to the present pharmaceutical composition. Biotin is involved in the metabolism of carbohydrates and fatty acids, which is necessary to cell growth. Furthermore, biotin aids in the utilization of glucose. Biotin is present in about 0.01 to 5 weight percent, preferably about 0.2 to 4 weight percent, and more preferably about 0.3 to 3 weight percent. A unit dose of biotin is typically about 0.2 mg to 40 mg, preferably about 0.4 mg to 30 mg, and more preferably about 0.6 mg to 20 mg.

The magnitude of a prophylactic or therapeutic dose of the composition in the treatment of acne damage to skin will vary with the sensitivity of the patient's skin and the route of administration. The dose, and perhaps the dose frequency, will also vary according to the age, body weight, and response of the individual patient. In general, the total daily dose range, for the conditions described herein, is from about 1 mg to about 2,500 mg per dose administered in 1 to 10 doses orally, more preferably 4 to 8 doses. The preferred unit dose range is preferably from about 400 mg to 2,000 mg, more preferably from about 800 mg to 1,600 mg per day. In a preferred form, the invention is used to treat acne and condition the skin cells. The oral formulation of the present invention may be used alone or in conjunction with other acne treatments.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient's response.

The terms "therapeutically effective amount of the composition" or "therapeutically effective amount of the pharmaceutically acceptable salt thereof" are encompassed by the above-described frequency and dosage amounts.

Although any suitable route of administration may be employed for providing the patient with an effective dosage of the composition according to the methods of the present invention, oral administration is preferred. Suitable routes include, for example, oral, rectal, parenteral, intravenous, topical, transdermal, subcutaneous, intramuscular, and like forms of administration may be employed. Suitable dosage forms include tablets, trochees, dispersions, suspensions, solutions, capsules, patches, suppositories, and the like, although oral dosage forms are preferred.

The pharmaceutical compositions used in the methods of the present invention include the active ingredients described above, and may also contain pharmaceutically acceptable carriers, excipients and the like, and optionally, other therapeutic ingredients.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example from N,N-dibenzylethylenediamine, chloroprocaine, choline, diethanolamine, ethylenediamine, meglumine (N-methylglucamine), and procaine.

The compositions used in the methods of the present invention include preparations such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets and capsules.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions for use in the methods of the present invention suitable for oral administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier with the active ingredient which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compressing or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet, cachet or capsule contains from about 0.1 mg to 2,500 mg of the active ingredients.

EXAMPLES

The invention is further defined by reference to the following examples, which describe in detail the preparation of the compound and the compositions used in the methods of the present invention, as well as their utility. The examples are representative, and they should not be construed to limit the scope of the invention.

Example 1 Capsules

A large number of unit capsules are prepared by filling standard two-piece hard gelatin capsules each with the desired amount of powdered active ingredients as described above, 150 milligrams of lactose, 50 milligrams of cellulose, and 6 milligrams magnesium stearate.

Example 2 Soft Gelatin Capsules

A mixture of active ingredients in a digestible oil, such as soybean oil, lecithin, cottonseed oil or olive oil, is prepared and injected by means of a positive displacement pump into gelatin to form soft gelatin capsules containing the desired amount of the active ingredient. The capsules are washed and dried for packaging.

Example 3 Tablets

A large number of tablets were prepared by conventional procedures to provide a dosage unit including: the desired amount of active ingredient as described herein, 5 milligrams of stearic acid, 4.26 milligrams of sorbitol, 1 milligram of acdisol, 0.5 milligrams of magnesium stearate, and 1.4 milligrams of syloid. Appropriate coatings may be applied, for example, to increase palatability or delay absorption. A specific therapeutic formulation of the active ingredients of the pharmaceutical composition prepared in tablet form is set forth in the table below:

These tablets are an example of a preferred embodiment of a unit dose according to the present invention.

Example 4 Effectiveness of Acne Composition

A study was conducted to determine the effectiveness of daily oral supplements prepared according to the tablet formulation of Example 3 and administered according present invention in reducing the incidence and severity of acne lesions. The study was conducted using fourteen panelists, although one did not finish due to non-study related reasons. Each of the panelists' complexion was evaluated using conventional methods known to those of ordinary skill in the art, e.g., the "Acne Grading Scale" for overall severity of Comedones, Papules, and Macules from the *Arch. Dermatol.*, Vol. 115 (May, 1979).

Prior to initiation of the study, each panelist was subjected to a global assessment of non-inflammatory and inflammatory lesions. All of the panelists exhibited grade two comedonal/inflammatory acne according to the Acne Grading Scale and were free from any skin disorders other than moderate acne. The panelists were instructed to take two tablets in the morning and two in the evening, preferably with meals, and record the administration time for the subsequent six weeks. In addition, the panelists were advised not to use any new cosmetics or facial products, including acne medications, while on the study.

The panelists returned after approximately 21 days and 42 days for an examination of the facial area to tabulate lesion counts and record the information on each panelist's score sheet. The study demonstrated that the daily use of tablets prepared according to the invention resulted in a statistically significant decrease in the number of acne lesions without any panelists reporting adverse reactions. The table below shows the results of the study.

| INGREDIENTS | MG PER TABLET | PERCENT BY WEIGHT | CHEMICAL OR SCIENTIFIC NAME |
|---|---|---|---|
| Vitamin E Succinate (63.1%) | 158.5 | 13.4% | D-alpha tocopheryl acid succinate |
| L-Lysine Hcl (80.0%) | 156.3 | 13.2% | L-Lysine hydrochloride |
| Calcium Ascorbate (81.0%) | 154.3 | 13.0% | Calcium ascorbate |
| Burdock Root | 150.0 | 12.7% | Arctium lappa |
| Yellow Dock | 125.0 | 10.6% | Rumex crispus polygonacae |
| L-Proline | 125.0 | 10.6% | L-Proline |
| Horsetail extract (Silica) | 100.0 | 8.4% | Equisetrum arvense |
| Magnesium Oxide (60.0%) | 83.3 | 7.0% | Magnesium oxide |
| Zinc Ascorbate (15.0%) | 25.0 | 2.1% | Zinc ascorbate |
| Vitamin $B_6$ (Pyridoxine HCL) (82.7%) | 15.1 | 1.3% | Pyridoxine hydrochloride |
| Grape Seed Extract | 12.5 | 1.1% | Proanthocyanidins |
| Vitamin $B_3$ (Niacin) | 12.5 | 1.1% | Niacinamide |
| Beta Carotene (yields 1,250 IU per tablet) | 10.0 | 0.9% | Beta carotene |
| Selenomethionine (0.5%) | 10.0 | 0.8% | L-selenomethionine |
| Biotin (1.0%) | 7.5 | 0.6% | Biotin |
| Vitamin $B_5$ (91.7%) | 6.8 | 0.6% | Pantothenic Acid |
| Vitamin $B_2$ (Riboflavin) | 6.3 | 0.5% | Riboflavin |
| Vitamin $B_1$ (Thiamine) | 6.3 | 0.5% | Thiamine |
| CHROMEMATE CHROMIUM GTF ™ (0.2%) | 6.3 | 0.5% | Chromium polynicotinate Chromium organically bound to nicotinic acid (niacin, vitamin $B_3$) |
| Vitamin A Palmitate (yields 1,250 IU per tablet) | 2.5 | 0.2% | Vitamin A palmitate |
| Chromium Picolinate (12.0%) | 0.1 | 0.01% | Chromium picolinate |

| Subject Number | Base-line | Mid-Point | Final | Mid-Point Baseline | Final Baseline | % Diff. Between Baseline Mid-Point and Final | |
|---|---|---|---|---|---|---|---|
| 1 | 38 | 22 | 20 | −16 | −18 | −42% | −47% |
| 2 | 45 | 18 | 10 | −27 | −35 | −60% | −78% |
| 3 | 38 | 40 | 27 | +2 | −11 | 5% | −29% |
| 4 | 32 | 21 | 13 | −11 | −19 | −34% | −59% |
| 5 | 41 | 6 | 9 | −35 | −32 | −85% | −78% |
| 6 | 35 | 23 | 17 | −12 | −18 | −34% | −51% |
| 7 | 52 | 20 | 20 | −32 | −32 | −62% | −62% |
| 8 | 46 | 23 | 16 | −23 | −30 | −50% | −65% |
| 10 | 31 | 16 | 15 | −15 | −16 | −48% | −52% |
| 11 | 29 | 21 | 12 | −8 | −17 | −28% | −59% |
| 12 | 39 | 16 | 14 | −23 | −25 | −59% | −64% |
| 13 | 39 | 26 | 15 | −13 | −24 | −33% | −62% |
| 14 | 19 | 31 | 17 | +12 | −2 | 63% | −11% |
| Mean | 37 | 22 | 16 | −15 | −21 | −36% | −55% |
| σ | 8.4 | 8.0 | 4.7 | 13.1 | 9.4 | | |

The first three columns of the table note the number of acne lesions on each of the panelists at the beginning, mid-point and end of the study. The difference in the number of acne lesions from the baseline and at both the mid-point of the study and the end of the study are noted in the next two columns of the table. The final columns disclose the percent difference in the number of acne lesions at both the mid-point and the end of the study.

As shown in the table at the mid-point evaluation, panelists exhibited a mean 36% decrease in total lesion count. Moreover, at the final examination, all of the subjects exhibited a decrease in the number of lesions, and the panelists exhibited a mean 55% decrease in the number of lesions.

Although preferred embodiments of the invention have been described in the foregoing Detailed Description of the Invention, it will be understood that the invention is not limited to the embodiments disclosed but is capable of numerous modifications without departing from the spirit and scope of the present invention. It will be understood that the chemical details may be slightly different or modified by one of ordinary skill in the art without departing from the methods and compositions disclosed and taught by the present invention.

What is claimed is:

1. A pharmaceutical composition for the treatment of acne comprising:
   an acne reduction component comprising at least one of a zinc compound in an amount greater than 15 mg to about 96 mg or a Vitamin A source in an amount sufficient to reduce the redness and blemishes associated with acne;
   at least one of burdock root yellow dock root, or a catechin-based composition in an amount sufficient to facilitate maintenance of skin cells; and
   a skin cell conditioning component comprising a transition metal other than zinc in an amount sufficient to properly regulate the keratin and sebum production of the skin cells to inhibit the appearance of acne.

2. The pharmaceutical composition of claim 1, wherein the transition metal is in the form of a transition metal complex.

3. The pharmaceutical composition of claim 2, wherein the transition metal complex comprises a transition metal complexed to a nitrogen containing aromatic compound.

4. The pharmaceutical composition of claim 3, wherein the transition metal is selected from Group IVB. Group VB, Group VIB, Group VIIB, or a mixture thereof and the complex is present in about 0.001 to 5 weight percent of the pharmaceutical composition.

5. The pharmaceutical composition of claim 1, wherein the acne reduction component further comprises a carotenoid component, a vitamin $B_6$ source, or both.

6. The pharmaceutical composition of claim 5, wherein the vitamin A source comprises vitamin A complexed with an acetate or palmitate, the carotenoid component comprises beta-carotene, the vitamin $B_6$ source comprises a pyridoxine, and the zinc component comprises zinc complexed with ascorbic acid or ascorbate.

7. The pharmaceutical composition of claim 6, wherein the vitamin A source is vitamin A palmitate present in about 0.005 to 5 weight percent, beta-carotene is present in about 0.1 to 10 weight percent, the pyridoxine is pyridoxine hydrochloride present in about 0.2 to 20 weight percent, and the zinc component is zinc ascorbate present in about 0.1 to 25 weight percent of the pharmaceutical composition.

8. The pharmaceutical composition of claim 1, wherein the composition further comprises a pharmaceutically acceptable carrier or excipient.

9. The pharmaceutical composition of claim 1, further comprising at least one of a vitamin C source, horsetail extract, a vitamin $B_1$ source, a vitamin $B_2$ source, a vitamin $B_3$ source, a vitamin $B_5$ source, and a vitamin E source, all in an amount sufficient to facilitate maintenance of skin cells.

10. The pharmaceutical composition of claim 9, wherein the vitamin C source comprises ascorbic acid or ascorbate, the catechin-based composition comprises a proanthanol or proanthocyanidin, the vitamin $B_1$ source comprises thiamin, the vitamin $B_2$ source comprises riboflavin, the vitamin $B_3$ source comprises niacinamide, the vitamin $B_5$ source comprises pantothenic acid, and the vitamin E source comprises a sulfate or succinate vitamin E complex.

11. The pharmaceutical composition of claim 10, wherein the vitamin C source is calcium ascorbate present in about 1 to 30 weight percent, the burdock root is present in about 1 to 30 weight percent, the yellow dock root is present in about 1 to 30 weight percent, the horsetail extract is present in about 1 to 20 weight percent, the catechin-based composition is proanthocyanidin present in about 0.1 to 15 weight percent, the niacinamide is present in about 0.05 to 5 weight percent, the pantothenic acid is present in about 0.05 to 5 weight percent, the riboflavin is present in about 0.05 to 5 weight percent, the thiamin is present in about 0.05 to 5 weight percent and the vitamin E source is vitamin E succinate present in about 1 to 30 weight percent.

12. The pharmaceutical composition of claim 1, further comprising at least one amino acid component, a magnesium component, a selenium component, and biotin in an amount sufficient to facilitate repair of skin damaged by acne.

13. The pharmaceutical composition of claim 12, wherein the amino acid component comprises L-lysine and L-proline, the magnesium component comprises magnesium oxide, and the selenium component comprises selenium complexed to an amino acid.

14. The pharmaceutical composition of claim 13, wherein the L-lysine is L-lysine hydrochloride, L-lysine and L-proline are together present in an amount from about 1 to 30 weight percent, magnesium oxide is present in about 1 to 20 weight percent, the selenium component is L-selenomethionine present in about 0.05 to 10 weight percent, and biotin is present in about 0.01 to 5 weight percent of the pharmaceutical composition.

15. A method for conditioning skin cells in a patient which comprises administering:

an acne reduction component comprising at least one of a zinc compound or a Vitamin A compound;

at least one of burdock root, yellow dock root, or a catechin-based composition in an amount sufficient to facilitate maintenance of skin cells; and a skin cell conditioning component comprising a transition metal other than zinc, said components administered in an amount therapeutically effective to regulate the keratin and sebum production of the skin cells and to reduce the redness and blemishes associated with acne.

16. The method of claim 15, wherein the composition is administered orally.

17. The method of claim 16, wherein the composition is administered as a tablet or capsule comprising about 1 mg to 2,500 mg of composition.

18. The method of claim 17, wherein the tablet or capsule comprises about 400 mg to 2,000 mg of composition.

19. The method of claim 18, wherein the tablet or capsule comprises about 800 mg to 1,600 mg of composition.

20. The method of claim 16, wherein the composition is administered in conjunction with concurrent or subsequent treatment by at least an additional pharmaceutical composition used to treat acne or condition the skin.

21. The method of claim 20, wherein the additional pharmaceutical composition is:

a topical application comprising at least one of: alcohol, benzoyl peroxide, erythromycin, clindamycin, tretinoin, vitamin E, and vitamin A or its derivatives; or an oral application comprising at least one of: erythromycin, tetracycline, isotretinoin, vitamin C, vitamin D, chaparral, dandelion root, licorice root, echinacea, kelp, cayenne, sassafras, elder flowers, pantothenic acid, para-aminobenzoic acid, biotin, choline, inositol, folic acid, calcium, magnesium, potassium and Vitamin A derivatives.

* * * * *